United States Patent [19]

Been

[11] 4,163,674

[45] Aug. 7, 1979

[54] PROCESS FOR MAKING A SYNTHETIC LIQUID ABSORBENT AND PRODUCTS RESULTING THEREFROM

[75] Inventor: Karl Been, Zuid, Netherlands

[73] Assignee: Oil-Dri Corporation of America, Chicago, Ill.

[21] Appl. No.: 783,792

[22] Filed: Apr. 1, 1977

Related U.S. Application Data

[62] Division of Ser. No. 683,090, May 4, 1976.

[51] Int. Cl.$^2$ ............................................. C09K 3/22
[52] U.S. Cl. .................... 106/15.05; 71/64 D; 106/109; 119/1; 252/88; 252/184
[58] Field of Search ............ 106/109, 15 R; 71/64 D; 252/88, 184, 190, 259.5; 119/1

[56] References Cited

U.S. PATENT DOCUMENTS

| | | | |
|---|---|---|---|
| 1,099,961 | 6/1914 | Barton | 252/259.5 |
| 2,253,755 | 8/1941 | Brant | 34/DIG. 1 |
| 2,805,204 | 9/1957 | Adams | 252/88 |
| 3,149,956 | 9/1964 | Seymour et al. | 71/64 D |
| 3,244,635 | 4/1966 | Duke | 252/88 |
| 3,673,095 | 6/1972 | Archer | 252/88 |
| 3,820,970 | 6/1974 | Watkins | 106/109 |
| 3,860,409 | 1/1975 | Wilson | 71/64 D |
| 3,921,581 | 11/1975 | Brewer | 119/1 |
| 4,048,337 | 9/1977 | Fabbian | 424/357 |

*Primary Examiner*—Lorenzo B. Hayes
*Attorney, Agent, or Firm*—Dressler, Goldsmith, Clement, Gordon & Shore, Ltd.

[57] ABSTRACT

A method for producing synthetic liquid absorbent granules to serve the same purposes as granules made from naturally occurring sorptive minerals such as absorbent clays. Water is mixed with powdered gypsum plaster in mixing apparatus and a paste or slurry condition results, with the volume of water relative to the plaster being varied to vary the bulk density and the absorption capacity characteristics of the ultimate granular product from each mix. The mix is taken from the apparatus and is allowed to set and harden in a form to be readily handled for crushing and sizing into desired screen mesh size granules, or the mix can be directly formed into pellets or granules so as to be allowed to set and harden and be correspondingly sized as the commercial product. Additives can be included in the mixing to vary the density and the absorption characteristics of the final absorbent granules. The fines recovered from screening and sizing the material can usually be introduced into the mix with the plaster and the water, whereby the otherwise unuseable fines have a useful function in the method and in the product manufactured thereby.

4 Claims, 1 Drawing Figure

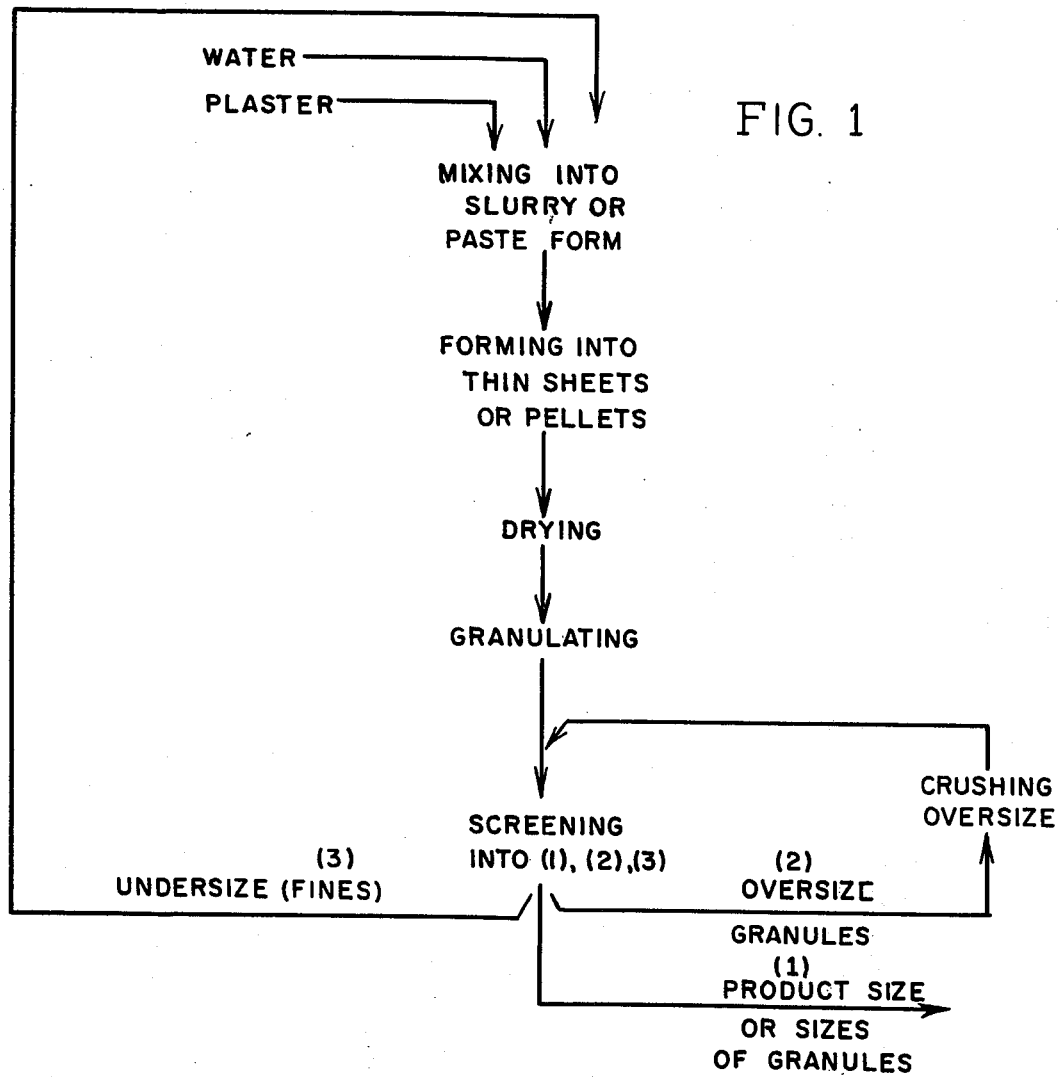

4,163,674

PROCESS FOR MAKING A SYNTHETIC LIQUID ABSORBENT AND PRODUCTS RESULTING THEREFROM

This is a division of application Ser. No. 683,090, filed May 4, 1976.

BACKGROUND OF THE INVENTION

1. Field of the Invention

The present invention relates to the field of absorbent granules produced from naturally occurring sorptive minerals, and in the past have consisted almost entirely of absorbent clay granules. The granules have various industrial and household uses such as the absorption of oil and grease and the like on floors and elsewhere where these materials represent a safety hazard, they are used in an animal toilet application as a cat box absorbent, they are used as a carrier for chemicals such as pesticides, herbicides and the like in various agricultural and horticultural applications, and they are used as ground cover in their natural color. The invention comprises a method for utilizing hydrated gypsum plaster. Gypsum as a naturally occurring mineral, or the powdered plaster therefrom, are not suitable as a moisture absorbent material such as is absorbent clay, but by controlled processing absorbent granules can be made with properties substantially equivalent to those of the absorbent clay granules.

More particularly, the present invention relates to a process utilizing standard commercially available plaster, or plaster of Paris as such plaster is often called, in powdered form made from gypsum. The plaster is mixed with water, or water and other materials, according to predetermined specifications for a mix. Variations in the specifications for the synthetic absorbent produce variations in the characteristics of the final absorbent granules produced thereby with respect to bulk density, moisture absorption, hardness, and stability in water or other liquid.

The absorbent granule product of this invention is consistent from mix to mix with respect to the specifications provided for the process, depending upon the plaster being the same from mix to mix, for it is known that plaster can vary in constituency. The characteristics of a plaster can be determined in advance of starting a production run so that adjustments can be made to compensate for undesired variations. Such consistency of product cannot be obtained in the manufacture of absorbent granules from the naturally occurring sorptive minerals such as the absorbent clays.

2. Description of the Prior Art

Beginning in the late 1930's and early 1940's, naturally occurring sorptive minerals, such as the clay which is known as fuller's earth, and having a natural porous structure, were first used as absorbents for oils, greases, water and other undesirable substances on the floors of factories and shops, filling stations, and the like. Prior to that, the major use of fuller's earth had been in the refining of oils. Because of the low bulk density of such material, in the range of 25 to 55 pounds per cubic foot, and because of its porosity and its absorbent properties, other uses were developed. Granules of fuller's earth found a large market as a use in pet animal toilet boxes, particularly cat boxes, and as a carrier for chemicals for agricultural purposes, as mentioned above. This density range represents what is considered to be a light weight material.

More specifically, as to the naturally occurring absorbent or sorptive mineral clays, these are mined, dried or calcined, crushed, and screened to a size determined by the particular use for which the material is intended.

For example, the usual size is 6×60 screen mesh for oil and grease absorbent, and for cat box absorbent. However, granules for each purpose can be of many different sizes, and 10×60 mesh, 6×16 mesh, and 6×24 mesh sizes have been marketed. A special size such as a very coarse 4×10 mesh has been used for either one of the above two purposes. For oil and grease absorbents, it is also desirable that the granules be resistant to crushing and to sticking to the floor when walked on, or travelled over by plant equipment such as lift trucks.

With respect to screen mesh sizes, the sizes for the two above discussed granules can vary quite widely, and larger size granules which are approximately 1 to 2 inches in diameter or in the cross dimension have been used for decorative ground cover.

For sorptive mineral clay granules when used as carriers for insecticides, or pesticides, or herbicides, the specifications are tight. Sizes which are commonly specified are 8×16, 16×30, 30×60, and 24×48, and each size has specified tolerances such as screen size, and bulk density. A representative specification for one such product is that the bulk density must be measured by the well known Ohaus Loose Bulk Density method, and such bulk density can be 31 to 35 lbs. per cu. ft. The screen size tolerance is that a maximum of 2% by weight of the granules can be larger than 20 mesh, and none larger than 10 mesh. There must not be any more than 1½% to 2% smaller by weight than 60 mesh for the granules. These mesh sizes are Tyler standards. In addition, it has been specified that there must be between 5 and 8 million particles or granules per pound of absorbent product.

For such chemical carriers, lack of dust in the product is important. It is also important that the specified properties of the absorbent clay granules be consistent from shipment to shipment since the distribution of the different chemicals by means of the granules is a carefully controlled operation.

From the above specific characteristics which are generally required, it is clear that a substantial degree of control should be maintained in processing the naturally occurring minerals such as absorbent clays in order to satisfy each of the numerous uses discussed for the granules. However, such control is not possible except by careful selection of the clay to be processed. Size can be varied by crushing and sizing, and the hardness and stability in water of the granules can be varied by calcining the sorptive mineral, but that is substantially the limit in the controlled variation of properties or characteristics of the absorbent granules made from naturally occurring minerals such as clay. There is no practical way to change the bulk density or the absorption capacity of such clays.

The lack of uniformity in bulk density in the clays at various mining and processing operations creates a problem in packaging. If the bulk density is high relative to the norm for a particular package size of granules, a predetermined amount such as 5 or 50 pounds will only partially fill a package or bag of a predetermined size. If the bulk density is too low or the clay is very light in weight relative to a norm, the package or bag will not accommodate the required weight of granules.

The usefulness and effectiveness of the absorbent clay granules for the purposes discussed above also vary with respect to the different mines in different locations from which the clay is obtained.

In addition to the preceding problems, absorbent clay as the principal sorptive mineral suitable for the purposes described is found only in limited areas in the United States and in some other countries of the world, and is not found at all in most industrial areas in the world. As a result, the cost of transportation overall from the sources of such clay to all the markets of the world is a substantial part of the total selling price. In fact, for the United States and perhaps even more so in Europe, the absorbent clay with the desired characteristics and suitable for the purposes described is found in such limited areas that a substantial percentage of the delivered cost of this bulky product is in its transportation cost.

With ever expanding use for the absorbent granules such as clay granules, and with the limited areas where such clay has been available, extensive searches for new sources of such raw materials have been undertaken by the industry. However, no substantial new deposits of sorptive minerals have been found which serve the same purposes as the absorbent clays, and no equivalent naturally occurring absorbent materials have been found which can be economically produced and marketed. Consideration has been given to synthetic substitutes, but until the product made by the process of the present invention was discovered, none has been found which has acceptable properties and characteristics, is competitive in cost, and for which the sources of supply are so located as to minimize the cost of transportation.

Considering that the need for such absorbents is world-wide, and the greatest need is in industrial, agricultural and urban areas, most of which are far removed from the sources of sorptive minerals such as absorbent clay, it is clear that the overall problems with this naturally occurring product have created hurdles for some time that the industry must surmount.

SUMMARY OF THE INVENTION

It is an object of the present invention to provide an essentially inorganic synthetic absorbent as a substitute for the naturally occurring sorptive minerals which can be granulated to a desired size for (1) use in absorbing liquids on the floors of factories, shops, and the like where water, oil, and grease accumulate and represent a safety hazard, (2) use as an absorbent in a cat box or other animal box, (3) use as an absorbent for carrying and distributing chemicals for agricultural applications, (4) use as a soil conditioner, and (5) use for light weight decorative ground cover to be colored with color pigments as desired.

It is also an object of my invention to provide a process to produce a granulated absorbent which can be practiced with materials which are available in many areas throughout the world so as to provide a ready source of supply of the granulated synthetic absorbent material relatively near the market for the same so that the cost of transportation of the manufactured product is materially reduced as compared to that cost for presently used absorbent granules.

A further object of my invention is to provide a process for making such an absorbent granule wherein the characteristics and the granule size of the ultimate product can be controlled to relatively tight specifications not only to insure that the product will serve the purposes for which it is intended, but that such characteristics of the product will be consistent from batch to batch made by the process.

A still further object is to provide a manufactured or synthetic absorbent as contrasted with the natural occurring absorbent that can be produced and marketed at a cost competitive with the natural product in a given location.

The principal feature of my invention is the provision of an absorbent granule product and a process for making the same, which product has the same purposes and is adapted for the same applications served by the absorbent granules made from naturally occurring sorptive minerals, and yet is plentiful in many areas throughout the world. The synthetic absorbent granule can be processed to controlled specifications on an economical basis, and the cost of transportation for many markets is reduced in comparison with that for the granules produced from naturally occurring sorptive minerals.

Plaster, or plaster of Paris as it is also called, from which the product of my invention is made, in turn, is manufactured from mined or quarried gypsum that is described chemically as calcium sulfate dihydrate ($CaSO_4.2H_2O$). In making the plaster, the raw gypsum is heated and loses water to form calcium sulphate hemihydrate ($CaSO_4.\frac{1}{2}H_2O$), or plaster. The manufacture of such plaster is well-known, and plants for such manufacture exist at many locations throughout the world.

My invention takes the plaster or calcium sulphate hemihydrate through steps which include mixing the plaster with water in predetermined quantities to form a slurry or a paste depending upon the amount of water used relative to the volume of plaster. The result of such step is that in time the plaster substantially reverts to gypsum ($CaSO_4.2H_2O$).

The slurry or paste is put into a form or forms for setting and hardening. After setting and hardening and drying the material is ground or crushed, and then screened to granules of the desired size. Or, as an alternative, the material is formed into predetermined configurations as granules. Such a mix is placed in a pelletizer or extruder or a similar device from which granules are prepared directly for the ultimate desired size.

The process can be practiced by readily available equipment for mixing and crushing and sizing, and as a result the process can be put into commercial practice in any location with a minimum of delay and at a minimum cost for a new manufacturing operation.

The ultimate absorbent granules are light in weight, have porous spaces therein for absorption of liquids, they maintain a satisfactory physical granular form in use, and they are chemically stable in those uses.

BRIEF DESCRIPTION OF DRAWINGS AND DESCRIPTION OF THE PREFERRED EMODIMENT

Referring now to the drawings:

FIG. 1 is a diagrammatic illustration of the steps in the process of my invention.

In practicing the process of the invention, commercially available plaster is placed in a mixer. Water is added to the powder in sufficient quantity to bring it to a paste or slurry condition during the mixing. The nature of the slurry or paste condition, in turn, is determinative of the ultimate density desired for the finished product.

A mix which is in slurry condition is normally poured into forms for setting and hardening. The mix in paste condition is either spread into a sheet-like form, or processed by machinery into pellets as cylinders or cubes, or into balls. The particular form of the material as processed from the paste condition is of a size and configuration to permit ready subsequent handling including crushing by equipment available for that purpose.

It is also noted that in the case of a pellet configuration for cat box absorbent, as one example of the use of such pellets, the paste can be processed so as to be formed into granules of the desired size which are ultimately used for the marketed product without any crushing.

The material is permitted to set and harden, and the timing to set and harden is affected by the use in the mixing step of known special plasters, retarders, or accelerators.

With the material in whatever form or configuration and size it is prepared for the setting and hardening step, it is allowed to set and harden, and is thereafter allowed to dry. Alternatively, it can be dried in a dryer, taking care, in any event, that the temperature in the dryer or in the environment in which it is dried does not exceed the dehydration temperature of the gypsum, which is approximately 250° F.–300° F. After the drying step, the material is then crushed, and thereafter screened to the desired granule size for the ultimate use of the product.

For some drying equipment, such as a fluid bed dryer, it may be desirable to first crush, then dry the granules, and thereafter screen the dried granules. This is not illustrated in FIG. 1.

As noted in FIG. 1, the purpose of the screening is to separate out those synthetic absorbent granules of the desired size for packaging and then marketing. The oversize granules are crushed or granulated again, and then run through the screens. The undersize particles are "fines" according to the sizing for that operation, and fines up to 30% by weight of the plaster in the mix are fed back into the mixing apparatus during the mixing step. The plaster and fines are mixed with water to a slurry or paste condition depending upon the amount of water used in the mix, and the succeeding steps as shown are carried out.

This use of the fines occurring in the practice of the present process is one of the advantages of this invention. There is no way to prevent fines from being formed in the crushing step, but here they can be used at little added cost and a resulting overall saving.

In the crushing and sizing operation of the natural mineral absorbent, such as absorbent clay, the members of the industry usually cannot recycle the fines or dust generated in such crushing and sizing. However, the assignee of the present application has pelletized such fines by a pelletizing operation disclosed in the pending application of Rudolph C. Valenta, Ser. No. 510,502, filed originally on Aug. 9, 1971, and assigned to such assignee. The alternative has been simply to dump or otherwise dispose of the clay fines.

In the above described preferred embodiment, the two characteristics of bulk density and moisture absorbency of the finished product of this present invention are controlled by varying the water content relative to the plaster. It is also possible to control such characteristics by including various additives in various amounts. The water content is varied in conjunction with the additive. Such additives are light weight naturally absorptive materials, as for example, paper pulp, or finely divided paper, or wood dust, peat dust, or light weight clay dust. Normally such additives are introduced into the mixing in the proportion of 1% to 20% of the weight of the plaster.

EXAMPLES

In practicing the preferred embodiment in Holland, the relative quantities of plaster and water were varied for the following representative batches, and the characteristics noted were obtained. The plaster utilized in all batches was identified as SBA 10FM, and it was obtained as a commerical product in Amsterdam, Holland.

| Batch No. | 1 | 2 | 3 | 4 | 5 | 6 |
| --- | --- | --- | --- | --- | --- | --- |
| Percent Plaster | 85 | 82 | 78 | 75 | 73 | 70 |
| Percent Water | 15 | 18 | 22 | 25 | 27 | 30 |
| Bulk Density (lbs/cu. ft.) | 50.5 | 51.8 | 48.3 | 41.1 | 38.8 | 38.7 |
| Water Absorption (Percent) | 22 | 19 | 24.7 | 27.4 | 34 | 33 |
| Set Time (Min.) | 8 | 8 | 11 | 13 | 14 | 14 |
| Batch No. | 7 | 8 | 9 | 10 | 11 | 12 |
| Percent Plaster | 68 | 66 | 63 | 62 | 60 | 58 |
| Percent Water | 32 | 34 | 37 | 38 | 40 | 42 |
| Bulk Density (lbs/cu. ft.) | 34.3 | 33.1 | 31.4 | 29.9 | 28.6 | 26.4 |
| Water Absorption (Percent) | 39.6 | 47 | 54.7 | 61.3 | 69.6 | 78 |
| Set Time (Min.) | 15 | 17 | 20 | 23 | 27 | 34 |

Such twelve batches varied in total weight from one pound to one and a half pounds, made up in plaster and water in the percentages by weight noted in the above table. Each batch was made by hand in a bowl and was removed from the bowl in which it was mixed and spread on a plastic sheet to a thickness of approximately one-quarter inch thick. After setting, the set piece was stable enough to be placed in a vertical position for air-drying. After such drying approximately one third of each set piece was broken into granules which were approximately 0.2 inch in size, and the granules were heated to 230° F. in hot air as the final drying step.

LARGE VOLUME BATCH EXAMPLE IN HOLLAND

Batch Number 7 appeared optimum for general use as ultimate absorbent granules from tests which were made for density and for water absorption, and the specification for that batch was selected for testing in a large volume. A total of one hundred ten pounds of the plaster described above and water were mixed in a commerical concrete mixer for 10 minutes. The proportion of this batch was 68% by weight of plaster and 32% by weight of water. The mix was poured from the mixer in the form of a layer approximately 1.2" thick, and after setting for approximately 3 hours, the material was hard and had a moisture content of 2.3%. The sheet was broken into small granules approximately 4×10 mesh screen in size.

Approximately 6.6 pounds of the small granules were spread on a greasy concrete floor to determine the capability or capacity of the granules as an oil and grease absorbent. After a period of approximately two hours, the oil and grease was absorbed by the granules, and on the following day these granules were removed simply by sweeping with a broom. The floor was dry and clean. The absorbent action was as good or better as that with the naturally occurring absorbent clay used for the same purpose.

Samples of 22 pounds each were used over a period of time in different cat toilet boxes, or cat boxes, as they are called, and the granules absorbed moisture and reduced odor in the respective boxes as satisfactorily as do the absorbent clay granules in a presently commercially available product.

EXAMPLES OF BATCHES MIXED IN THE UNITED STATES

Plaster and water batches were also mixed in the United States with U.S. Gypsum No. 1 Moulding Plaster obtained in Chicago, Ill., and each batch was made by putting the plaster and water into a commercially available electric kitchen mixer and bowl. Each mix was 1 to 1½ pounds in total weight. After mixing, the material was placed or poured, depending on the consistency of the material as mixed, onto a plastic sheet and allowed to set and harden for one hour. Each sheet was then broken into pieces and placed in front of a blower of hot air at 100° F. and dried for three hours.

The broken pieces were then granulated in a hand operated grinder and the granules were sized by screening with a 6 mesh screen, and with a 16 mesh screen. The granules which passed through the 6 mesh screen were then placed on a 16 mesh screen for passing through that screen or being retained on the screen. Three sizes were obtained by this sizing, (1) those that did not pass through the 6 mesh screen, (2) those that passed through the 16 mesh screen, and (3) those that passed through the 6 mesh but were retained on the 16 mesh size screen.

Those that did not pass through the 6 mesh screen (No. 1 above) were recrushed to a size so that they would pass through the 6 mesh screen. After this crushing, the granulated material was 6×16 mesh sizes, and that smaller than 16 mesh was classified as "fines" and was not further tested. In other words, as is the practice in the liquid absorbent granule industry, those granules passing through the finest screen size used in the operation which are not destined for marketing in that particular manufacturing operation at a particular time are called "fines".

The 6×16 mesh material (this passed the 6 mesh screen but did not pass through the 16 mesh screen) was tested for bulk density, for liquid absorption, and for oil absorption. The tests for determining the absorption characteristics of the granules are those specified in Bulletin P-A-1056, Federal Specification, Absorbent Material, Oil and Water (For Floors and Decks), to be obtained from General Services Administration. The batches, and the results of the testing are summarized:

| Batch No. | 13 | 14 | 15 | 16 | 17 |
|---|---|---|---|---|---|
| Percent Plaster | 70 | 62 | 59 | 56 | 50 |
| Percent Water | 30 | 38 | 41 | 44 | 50 |
| Bulk Density lbs/cu.ft. | 48 | 38.6 | 38 | 35.5 | 33 |
| Percent Water Absorption | 52 | 50 | 66 | 70 | 88 |
| Percent Oil Absorption | 34 | 50 | 58 | 66 | 74 |

Note 1 - Batch No. 1 was in paste form; all others were in slurry form.

The above data shows these batches to be well within the range of characteristics for commercially accepted granulated clay absorbents now in use, which are as follows:

|  | Commercial Range | Range or Size From The Above Batches 13 to 17 Inclusive |
|---|---|---|
| Bulk Density | 20-55 lbs/cu. ft. | 33-48 |
| Oil and Water Absorption | 20-110% | 30-88% |
| Mesh Size | 6 × 60 | 6 × 16 |

EXAMPLE OF BATCHES WITH ADDITIVE TO THE MIX

Mixes were also made in Holland with the plaster purchased in Amsterdam under the identification SBA 10FM, and with used newspaper as an additive to the mixture to aid in varying the bulk density and absorption capacity characteristics of the ultimate synthetic absorbent granules. The used newspaper was reduced to a sludge or pulp by mixing with water in a high speed electric mixer. Excess water was pressed out of the mix so the paper water ratio was 1:15 when ready to be mixed with the plaster and water.

The used newspaper treated as above was mixed with the plaster and water in proportions shown in the following table with the density and water absorption characteristics of each of the six batches or mixes. Each batch was approximately 1 pound to 1.5 pounds, and was mixed by hand, and removed, set and hardened, dried, and then granulated in the same manner as described above for the twelve batches made in Holland.

| Batch No. | 18 | 19 | 20 | 21 | 22 | 23 |
|---|---|---|---|---|---|---|
| Percent Plaster | 69.6 | 66.7 | 64.5 | 64 | 61.5 | 59.3 |
| Percent Paper | .9 | 1.7 | 1.6 | 2.4 | 3.1 | 3.7 |
| Percent Water | 29.5 | 31.6 | 33.9 | 33.6 | 35.4 | 37.0 |
| Density (lbs/cu.ft.) | 33.7 | 32.6 | 29.5 | 28.1 | 25.7 | 24.4 |
| Percent Water Absorption | 44.6 | 51.2 | 58 | 73 | 81 | 111 |
| Setting Time (Min.) | 16 | 19 | 20 | 24 | 30 | 31 |

Note: Percentage of paper is measured on basis of the weight of dry paper.

Samples of 22 pounds each from the formulation of batches 20 and 21 were tested in cat boxes over a period of time, and the synthetic absorbent granules from each batch served their purpose very satisfactorily.

TESTING TO DETERMINE PLASTER CHARACTERISTICS FOR PRODUCTION OF SYNTHETIC ABSORBENT GRANULES

Plaster characteristics may vary for numerous reasons including the location and nature of the gypsum mined, as well as the actual manufacturing specifications for the plaster. In order to determine the synthetic absorbent granule characteristics for a given plaster, simple tests can be made corresponding to the formulations and the procedures for any one or more of Batches 1 to 17 inclusive above. The water content for a test batch will determine the bulk density and absorption characteristics for that batch. When the desired characteristics are obtained, that is the water content to use for production of granules using that particular plaster. The various examples indicate that a simple test will determine in advance the water content to be used with an plaster in order to meet a particular specification for the granules.

If additives, such as paper pulp or other light weight naturally absorptive materials are to be used, the examples in Batches 18 to 23 inclusive illustrate corresponding test methods for checking the combination of plaster and each such absorptive material to obtain the desired characteristics for the final granules to be used for absorbing purposes.

If it is desired to have synthetic colored granules in accordance with the present invention, pigment of the desired color is mixed with the material in the mixing apparatus including plaster and water. The entire batch of the desired color is then processed through the remaining steps described herein, and crushed and granulated to the desired screen mesh size.

Accordingly, the process of the present invention shows that liquid absorbent granules can be synthesized to provide equivalent or improved characteristics relative to the granules made from naturally occurring liquid absorbent minerals such as fuller's earth, and such characteristics can be controlled to a predetermined formulation for a particular purpose in a manner and to a degree not possible with the natural product.

I claim:

1. Synthetic liquid absorbent material in a granule form and having absorbent properties substantially equivalent to those of absorbent clay granules, said synthetic granules adapted to be used for any one of different liquid absorption purposes including that as an oil and grease absorbent on floors or the like, that as an absorbent in toilet boxes for household pets, that as an absorbent to carry a chemical to be used as an insecticide, or herbicide, or fungicide for agriculture purposes, and that as a ground cover or a conditioner, said material comprising gypsum granules manufactured by crushing a combination of set and hardened materials derived from a mixture containing gypsum plaster and water in an amount of about 15 weight percent water and about 85 weight percent plaster to about 50 weight percent water and about 50 weight percent plaster to provide hardened granules having a bulk density of about 26.4 to about 51.8 lbs./ft$^3$, water absorption of about 19 percent to about 88 percent, and oil absorption of about 34 percent to about 74 percent.

2. The synthetic liquid absorbent material in a granule form as defined in claim 1 which includes as an additive therein about 1 to about 20 percent by weight of the plaster of a light weight naturally absorptive material selected from the group consisting of paper pulp, finely-divided paper, wood dust, and clay dust that affects the bulk density of the granules.

3. A synthetic liquid absorbent material as defined in claim 2, wherein the light weight naturally absorptive material is used-newspaper.

4. A synthetic liquid absorbent material as defined in claim 2, wherein the light weight naturally absorptive material is clay dust.

* * * * *